drugs, either orally or by other routes, in such dosage forms as injections, capsules, powders, granules, tablets and so on which may be prepared in manners known per se. The carrier used in the preparation of such injections may for example be distilled water or physiological saline. To prepare said capsules, powders, granules or tablets, compound (I) is used in admixture with pharmaceutically acceptable excipients known per se (e.g. starch, lactose, sucrose, calcium carbonate, calcium phosphate, etc.), binders (starch, gum Arabic, carboxymethyl-cellulose, hydroxypropyl-cellulose, crystalline cellulose, etc.), lubricants or mold releases (e.g. magnesium stearate, talc, etc.) and disintegrating agents (e.g. carboxymethyl calcium, talc, etc.), for instance.

Thus, the compound (I) is a novel and safe low-toxicity compound which is β-lactamase-resistant, and displays excellent activity against a broad spectrum of microorganisms including Gram-negative bacteria such as *Escherichia coli, Serratia marcescens, Proteus rettgeri, Enterobacter cloacae, Citrobacter freundii*, etc. Therefore, compound (I) can be used as a disinfectant for the removal of said microorganisms, or as a therapeutic agent for the treatment of infectious diseases.

Among various compounds of formula (I), sodium 7-[2-(2-aminothiazol-4-yl)-2-(syn)-methoxyiminoacetamido]-3-(5-acetamido-1,3,4-thiadiazol-2-yl)-3-cephem-4-carboxylate; 7-[2-(2-aminothiazol-4-yl)-2-(syn)-methoxyiminoacetamido]-3-(5-dimethylamino-1,3,4-thiadiazol-2-yl)-3-cephem-4-carboxylic acid or its sodium salt; 7-[2-(2-aminothiazol-4-yl)-2-(syn)-methoxyiminoacetamido]-3-(5-methyl-1,3,4-thiadiazol-2-yl)-3-cephem-4-carboxylic acid or its sodium salt; 7-[2-(2-aminothiazol-4-yl)-2-(syn)-methoxyiminoacetamido]-3-(1,3,4-thiadiazol-2-yl)-3-cephem-4-carboxylic acid; 7-[2-(2-aminothiazol-4-yl)-2-(syn)-methoxyiminoacetamido]-3-(5-acetamido-1,3,4-triazol-2-yl)-3-cephem-4-carboxylic acid or its sodium salt; 7-[2-(2-aminothiazol-4-yl)-2-(syn)-methoxyiminoacetamido]-3-(5-acetamido-1,3,4-oxadiazol-2-yl)-3-cephem-4-carboxylic acid or its salt, for instance, can be safely administered, e.g. for the treatment of infectious diseases such as intraperitoneal infections, respiratory organ infections and urinary tract infections, to mammals including human beings, mice and rats at a daily dose level of 0.5 to 80 mg or, preferably, 1 to 20 mg per kilogram body weight in 3 to 4 divided doses a day.

EXAMPLE 1

In 5 ml of methylene chloride is suspended 133 mg of 2-(2-chloroacetamidothiazol-4-yl)-2-methoxyiminoacetic acid (syn-isomer), followed by addition of 59 mg of triethylamine and, then, 100 mg of phosphorus pentachloride. The reaction is conducted with stirring at room temperature for 20 minutes. To the reaction mixture is added 20 ml of n-hexane and the oily substance obtained by decanting the supernatant is dissolved in 3 ml of methylene chloride. This acid chloride solution is added dropwise to 3 ml of N,N-dimethylacetamide containing 202 mg of diphenylmethyl 7-amino-3-(5-acetamido-1,3,4-thiadiazol-2-yl)-3-cephem-4-carboxylate and the mixture is stirred for 2 hours. Water is added to the reaction mixture which is then extracted with ethyl acetate. The ethyl acetate layer is washed with water, dried and concentrated. By the above procedure is obtained 145 mg of crude diphenylmethyl 7-[2-(2-chloroacetamidothiazol-4-yl)-2-methoxyiminoacetamido]-3-(5-acetamido-1,3,4-thiadiazol-2-yl)-3-cephem-4-carboxylate as powders.

100 mg of the above product is dissolved in 1.5 ml of N,N-dimethylacetamide, followed by addition of 25 mg of thiourea. The mixture is stirred at room temperature for 18 hours. The reaction mixture is added to water and extracted with ethyl acetate. The ethyl acetate layer is washed with water, dried and concentrated. The above procedure yield, diphenylmethyl 7-[2-(2-aminothiazol-4-yl)-2-methoxyiminoacetamido]-3-(5-acetamido-1,3,4-thiadiazol-2-yl)-3-cephem-4-carboxylate. The entire amount of this product is dissolved in 5 ml of trifluoroacetic acid containing 1 ml of anisole and stirred at room temperature for 30 minutes. The reaction mixture is poured into ether and the solid precipitate is collected by filtration. This is dissolved in 0.5 ml of water and the solution is adjusted to pH 7.0 with sodium hydrogen carbonate and purified by passing through a column of Amberlite XAD-2. By the above procedure was obtained 29 mg of sodium 7-[2-(2-aminothiazol-4-yl)-2-methoxyiminoacetamido]-3-(5-acetamido-1,3,4-thiadiazol-2-yl)-3-cephem-4-carboxylate as white powders.

Elemental analysis, for $C_{17}H_{15}N_8O_6S_3Na.4.5\ H_2O$: Calcd. C, 32.53; H, 3.85; N, 17.85: Found C, 32.19; H, 3.29; N, 17.14.

NMR spectrum (60 MHz, in $D_2O$): 2.26 ppm(3H, singlet, $COCH_3$), 4.02 ppm(5H, broad singlet, 2-$CH_2$ & $OCH_3$), 5.37 ppm (1H, doublet, 6-H), 5.92 ppm(1H, doublet, 7-H), 7.01 ppm (1H, singlet, thiazole 5-H).

REFERENCE EXAMPLE 1

To 200 ml of water is added 38 g of sodium nitrite together with 53 g of methyl acetoacetate, followed by dropwise addition of 200 ml of 4 N-sulfuric acid under ice-cooling and stirring over a period of about an hour. During this period, the temperature of the reaction mixture is maintained at 5° to 8° C. The mixture is further stirred within this temperature range for 2.5 hours, at the end of which time it is extracted twice with each 300 ml of ethyl acetate. The extracts are washed twice with a saturated aqueous solution of sodium chloride. Then, a solution of 96.7 g of sodium carbonate in 1 l of water is divided in three parts, which are used to extract methyl 3-oxo-2-hydroxyiminobutyrate from the ethyl acetate layer previously obtained as above (3 times). To the water layer (1 l) was added 200 ml of methanol and, under ice-cooling and stirring, 150 g of dimethyl sulfate is added dropwise over a period of 10 minutes. After the dropwise addition has been completed, the mixture is stirred at room temperature for 1.5 hours. It is then extracted twice with each 300 ml of ethyl acetate, dried and distilled to remove the ethyl acetate. The residue is cooled with ice, whereupon it solidifies. This solid is collected by filtration and rinsed with a small quantity of water. By the above procedure is obtained 52.3 g of methyl 3-oxo-2-methoxyiminobutyrate as white crystals melting at 64.4° C.

Elemental analysis, for $C_6H_9NO_4$: Calcd. C, 45.28; H, 5.70; N, 8.80: Found C, 44.93; H, 5.61; N, 8.71.

NMR spectrum (60 MHz, in $CDCl_3$): 2.40 ppm

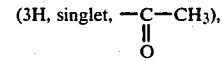
(3H, singlet, $-\overset{\overset{\displaystyle O}{\|}}{C}-CH_3$), 3.86 ppm(3H, singlet, $COOCH_3$), 4.10 ppm(3H, singlet, $=NOCH_3$)

United States Patent [19]

Ferrari et al.

[11] 4,197,299

[45] Apr. 8, 1980

[54] ANTI-HYPERTENSIVE DERIVATIVES OF ERGOLINE-2-THIOETHERS AND THEIR SULPHOXIDES

[75] Inventors: Giorgio Ferrari; Vittorio Vecchietti, both of Milan, Italy

[73] Assignee: Simes Societa Italiana Medicinali e Sintetici, Milan, Italy

[21] Appl. No.: 917,335

[22] Filed: Jun. 20, 1978

[30] Foreign Application Priority Data

Jul. 5, 1977 [CH] Switzerland ................ 8255/77

[51] Int. Cl.$^2$ .............. A61K 31/55; A61K 31/48; C07D 457/04; C07D 457/02
[52] U.S. Cl. ..................... 424/248.52; 424/248.5; 424/250; 424/261; 544/125; 544/346; 544/361; 546/67; 546/69
[58] Field of Search ............ 544/125, 346, 361; 260/285.5, 293.54; 424/261, 250, 248.5, 248.52; 546/69, 67

[56] References Cited

U.S. PATENT DOCUMENTS

| | | |
|---|---|---|
| 3,324,133 | 6/1967 | Arcamone et al. ............ 544/346 |
| 3,752,814 | 8/1973 | Fluckiger et al. ............ 544/346 |
| 3,901,894 | 8/1975 | Kornfeld et al. ............ 260/285.5 |
| 3,920,664 | 11/1975 | Clemens et al. ............ 260/285.5 |

OTHER PUBLICATIONS

Fusco–Bianchetti, Chimica Organica II, p. 584.
Kirk–Othmer, Encyclopedia of Chemical Technology, vol. 7, Interscience, New York, 1951, p. 840.
Kharasch, N., *Organic Sulfur Compounds*, vol. 1, Pergamon Press, New York, 1961, pp. 382–383.
Dryhurst, G., *Periodate Oxidation of Diol and Other Functional Groups,*, Pergamon Press, Oxford, 1966, pp. 61–64.

*Primary Examiner*—Henry R. Jiles
*Assistant Examiner*—Richard A. Schwartz
*Attorney, Agent, or Firm*—Cushman, Darby & Cushman

[57] ABSTRACT

A method for preparing ergoline derivatives in which the ergoline structure is variously substituted by morpholino-piperazino- and other active radicals to obtain novel compounds useful in cardiology as alpha-blocking, vasodilating, antihypertensive active ingredients of pharmaceutical preparations.

10 Claims, No Drawings

ANTI-HYPERTENSIVE DERIVATIVES OF ERGOLINE-2-THIOETHERS AND THEIR SULPHOXIDES

The present invention concerns new ergoline derivatives of formula I and their use as pharmaceutically acceptable products

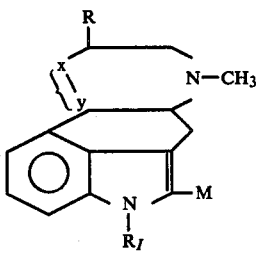

wherein R=CH$_2$—OH,

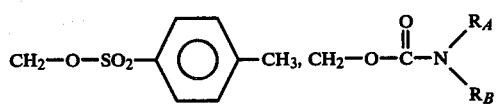

(where R$_A$ and R$_B$ are alkyls (C$_1$-C$_4$) straight or branched, or R$_A$ is simply linked to R$_B$ to form heterocycles, with C$_3$-C$_8$ carbon atoms, e.g.

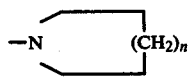

or linked with insertion of heteroatoms to form heterocycles

such as morpholine (Z=O) and piperazine (Z=NH or N—R$_{III}$, where R$_{III}$=alkyl C$_1$-C$_4$, phenyl) COOCH$_3$,

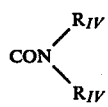

(where R$_{IV=H}$, alkyl C$_1$-C$_6$), CH$_2$—CN,

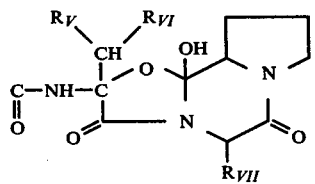

(where R$_V$=R$_{VI}$=H or R$_V$=R$_{VI}$=CH$_3$

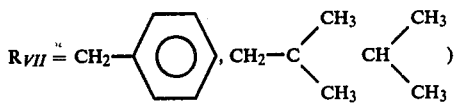

M=S—R$_{II}$ or SO—R$_{II}$
R$_I$=H, alkyl C$_1$-C$_4$
R$_{II}$=alkyl (C$_1$-C$_6$), phenyl
x̄ ȳ=CH$_2$—CH<, CH=C<.

It has been found that the new compounds of general formula I, wherein M=S—R$_{II}$ can be prepared by reacting ergolines which are not substituted at position 2 with sulphochlorides such as R$_{II}$—S—Cl (where R$_{II}$ is the above identified group) in aprotic solvents, such as methylene chloride, chloroform, dichloroethane, tetrahydrofuran, ethylene glycol dimethylether, etc., in a temperature range from −75 to +25° C., possibly in the presence of acid acceptors, such as NaHCO$_3$, Na$_2$CO$_3$, K$_2$CO$_2$, triethylamine, propyleneoxide. The reaction products can be separated and purified with usual methods such as for example crystallization, column chromatographic separation on SiO$_2$, Al$_2$O$_3$, etc. Separation, purification and yield are greatly simplified and improved when the reaction products are treated with Raney Ni in alcoholic solvents such as methanol, ethanol, in a temperature range from 25° C. to 150° C. to eliminate all the labile secondary products of polysubstitution.

Furthermore, it has been found that the compounds of general formula I where M=SO—R$_{II}$ can be prepared by oxidizing the corresponding sulphurated compounds M=S—R$_{II}$ with, for example, NaIO$_4$ in aqueous dioxane or acetontrile or methanol, or with N-chlorobenzotriazole in solvents such as methylene chloride, CHCl$_3$, tetrahydrofuran, methanol, or mixtures thereof, at low temperature (from −75° C. to −30° C.).

The compounds of general formula I are generally solid, crystalline and provide pharmaceutically acceptable salts with inorganic acids such as hydrochloric, hydrobromic, sulphuric, phosphoric acid, or organic acids, such as maleic, tartaric, citric, methansulphonic, etc.

The new compounds can be used as drugs as such or in the form of suitable salts with pharmaceutically acceptable acids, in doses of 0.1-10 mg.

The pharmaceutical dosage form can be tablets, sugar-coated tablets, drops, vials, suppositories. The solid forms for oral use can be formulated by mixing the active ingredient with various vehicles and diluents, such as lactose, mannitol, starch, cellulose and derivatives thereof, and lubricants such as magnesium or calcium stearate. The mixtures so obtained as treated to provide tablets or cores and these latter can be subsequently coated with sugar containing gum arabic, talc and a suitable lake or dye.

Or else, the said pharmaceutical product can be formulated as hard or soft gelatin capsules. In the soft gelatin capsules the active ingredient is preferably dissolved or suspended in a suitable liquid such as polyoxyethyleneglycol in the presence of a stabilizer such as sodium metabisulphite or ascorbic acid. In this way it is possible also to provide a pharmaceutical dosage form with prolonged release over time (sustained release form).

Finally, for rectal use, the active ingredient can be formulated for example in gelatin capsules for rectal use or with a vehicle for suppositories, for instance natural triglycerides such as cocoa butter.

The solution for parenteral use or the drops for oral use can be prepared by dissolving the active ingredient as such or in the form of a salt in a suitable dissolving and stabilizing agent comprising for example only sterile water or water containing 5–20% of ethanol, glycerol, propyleneglycol.

The following Examples illustrate the invention though without any way limiting it:

EXAMPLE 1

3 g of methyldihydrolysergate in 100 ml of $CHCl_3$ is cooled to $-60°$ C. with dry ice and treated under agitation with 1.32 g of freshly distilled $CH_3$—S—Cl. The mixture is left under agitation for 30′ at $-60°$ C. then the temperature is allowed to increase to $-5°$ C. and a basic pH is obtained with 5% $NH_4OH$. The organic phase is separated, washed with water to neutrality, then concentrated to dryness. The residue is chromatographed on a column of $SiO_2$ disactivated with 10% $H_2O$, eluting with $CH_2Cl_2/MeOH$ 99:1. The purified product is crystallized from benzene thus obtaining 1.9 g of methyl-2-methylthio-dihydrolysergate (compound 1); m.p. 188–190 $[\alpha]-15.3$ (c=0.5 $C_5H_5N$) $\lambda_{max}^{MeOH}$ 295 m$\mu$ flex ($\epsilon$ 12.120) 290 m$\mu$ ($\epsilon$13.500) 226 m$\mu$ ($\epsilon$29.200); M+330; $C_{18}H_{22}N_2O_2S$ calc. 65,42; %H 6.71; %N 8.48; found %C 64.35; %H 6.43; %N 8.33. The compounds from 7 to 17 are prepared similarly.

EXAMPLE 2

1.5 g of D-6-methyl-8beta (perhydroazepinyl-carbonyloxymethyl) didehydro-ergoline in 100 ml of methylene chloride is cooled to $-30°$ C. and 0.86 g of phenylsulphochloride is added. Leave at $+4°$ C. for 18 hrs., then quench with 5% $NH_4OH$; the organic phase is separated, washed with water to neutrality, then concentrated to dryness. The oily residue is dissolved in 99% EtOH and treated with 0.42 g of Maleic acid. The maleate is twice crystallized from 99% EtOH thus obtaining 1.15 g, of D-6-methyl-2-phenylthio-8beta (perhydroazepinyl carbonyloxymethyl)-didehydro-ergoline maleate (compound 2); m.p. 213–5 $[\alpha]-11$ (c=0.5 $C_5H_5N$) $\lambda_{max}^{MeOH}$ 314 m$\mu$ ($\epsilon$14.900) 252–242 m$\mu$ flex, 213 m$\mu$ ($\epsilon$39.000); M+487 $C_{33}H_{37}N_3O_6S$ calc. %C 65.55; %H 6.18; %N 6.96; found %C 65.20; %H 6.06; %N 6.63. D-6-methyl-z-phenylthio-8beta (perhydroazepinil carbonyloxymethyl)-ergoline (compound No. 20) is similarly prepared.

EXAMPLE 3

To 4.2 g of hydroergocristine in 250 ml of chloroform cooled to $-60°$ C. there is added 1.8 g of freshly distilled $CH_3SCl$. It is left under agitation, until a chromatographic control shows that there is no longer any dihydroergocristine. The solution is quenched with 5% $NH_4OH$, the organic phase is separated, washed to neutrality, then dried. The residue is dissolved in 250 ml methanol and treated under reflux with Raney Nickel in portions for a total of 35 ml. After boiling for 2 hrs., the reaction is complete. Cool, filter to separate Nickel and concentrate to dryness. The residue is chromatographed on $SiO_2$, disactivated with 10% $H_2O$, by eluting with $CH_2Cl/MeOH$ 99:1 and 95:5. The homogeneous fractions are collected, dissolved in acetone, and there is added methansulphonic acid to obtain an acid reaction. The salt is completely precipitated with anhydrous ether, the solid is filtered and crystallized from ethyl acetate obtaining 3.5 g of 2-methylthio-dihydro ergocristine methansulphonate (compound 3); m.p. 186–9 $[\alpha]-60$ (c=0.5 $C_5H_5N$) $\lambda_{max}^{MeOH}$ 290 m$\mu$ ($\epsilon$13.800) 220–4 flex 208 m$\mu$ ($\epsilon$36.300) $C_{37}H_{47}N_5O_8S_2.1$ $H_2O$—calc; %C 57.57; %H 6.39; %N 9.07—found %C 57.01; %H 5.81; %N 8.93.

EXAMPLE 4

To 2 g of D-6-methyl-2-methylthio-8beta(perhydroazepinyl-carbonyloxymethyl) ergoline in 200 ml acetonitrile, maintained at 50° C., there is added over 3 hours 4.5 g sodium metaperiodate, dissolved in 30 ml $H_2O$ at 50°–60° C. for 6 hrs, then dilute with water and extract with $CHCl_3$. The $CHCl_3$ residue is chromatographed on $SiO_2$ disactivated with 10% water, eluting with $CH_2Cl/MeOH$ 99:1–80:20. The homogeneous fractions are collected and crystallized from $CH_3COOEt$ thus obtaining 0.70 g of D-6-methyl-2-methylsulphonyl-8beta(perhydroazepinyl carbonyloxymethyl) ergoline (compound 4); m.p. 230°–2° C. $[\alpha]-73$ (c=0.5 $C_2H_5N$) $\lambda_{max}^{MeOH}$ 286 m$\mu$ ($\epsilon$17.800) 226 m$\mu$ ($\epsilon$26.500) 214 m$\mu$ ($\epsilon$21.400); M+ 443; $C_{24}H_{33}N_3O_3S$ calc. %C 64.98; %H 7.50; %N 9.47; found %C 65.23; %H 7.56; %N 9.36.

EXAMPLE 5

2 g of D-6-methyl-2-methylthio-8beta(dimethylamino carbonyloxymethyl) ergoline, dissolved on 50 ml of a mixture $CH_2Cl_2/MeOH$ 4:1 is cooled to $-60°$ C. and treated with 0.82 g of 1-chlorobenzotriazol, dissolved in 10 ml $CH_2Cl_2/MeOH$ 1:1. After agitation for 2 hrs at $-20°$ C., 25 ml of 1 N NaOH, is added, the organic phase is separated and the water phase is extracted with $CH_2Cl_2$. After drying and concentrating the organic phase, the residue is chromatographed in order to carry out a partial purification, on $SiO_2$, by eluting with $CH_2Cl_2/MeOH$ 99:1 and 95:5. The crude material is further purified by chromatography on acid $Al_2O_3$ (IV) again eluting with $CH_2Cl_2/MeOH$ 99:1. After crystallization from $CH_3COOEt$, D-6-methyl-2-methylsulphonyl-8beta(dimethylaminocarbonyloxymethyl)ergoline (compound 5) 0.45 g is obtained; m.p. 233–5 $[\alpha]-73$ (c=0.5 $C_5H_5N$)$\lambda_{max}^{MeOH}$ 286 m$\mu$ ($\epsilon$17.000) 228 m$\mu$($\epsilon$25.400) 214 m$\mu$ ($\epsilon$19.000) M+389 $C_{20}H_{27}N_3O_3S$ calc. %C 61.67; %H 6.99; %N 10.79; found %C 62.37; %H 6.85; %N 10.68. The compounds Nos. 18 and 19 are prepared similarly.

The compounds claimed in the present invention show interesting pharmacological properties, evidenced by means of classical tests on laboratory animals at extremely low doses.

In particular, the new compounds show alpha-blocking and vasodilator, anti-hypertensive, anti-serotonic both peripheral and central- and anti-asthmatic, anti-depressive and, in two cases, analgesic properties. In particular, compounds 11 and 9 have a broad spectrum of pharmacologycal properties, shown in the following table, compared to known substances used as comparison.

| | (a) in vitro $EC_{50}$ ng/ml | Antiadrenalin activity in vivo (b) $ED_{50}$ $\mu$g/kg/iv | Anti $BaCl_2$ activity (e) $EC_{50}$ $\mu$g/ml | Anti 5HT activity in vitro (f) $EC_{50}$ ng/ml | Antitriptanic activity in vivo (g) $ED_{50}$ mg/kg/sc |
|---|---|---|---|---|---|
| 11* | 1.3 | 18.8 | 10 | 0.01 | 0.05 |